United States Patent [19]

Vlasbloem

[11] Patent Number: 5,008,915
[45] Date of Patent: * Apr. 16, 1991

[54] METHODS FOR FORMING A RADIOGRAPH USING SLIT RADIOGRAPHY

[75] Inventor: Hugo Vlasbloem, Maasland, Netherlands

[73] Assignee: B.V. Optische Industrie "De Oude Delft", Delft, Netherlands

[ * ] Notice: The portion of the term of this patent subsequent to Dec. 22, 2004 has been disclaimed.

[21] Appl. No.: 306,348

[22] Filed: Feb. 3, 1989

Related U.S. Application Data

[63] Continuation-in-part of Ser. No. 648,707, Sep. 7, 1984, Pat. No. 4,803,714.

[30] Foreign Application Priority Data

Sep. 13, 1983 [NL] Netherlands .......................... 8303156

[51] Int. Cl.[5] .............................................. G01N 23/04
[52] U.S. Cl. ...................................... 378/108; 378/62; 378/145
[58] Field of Search ................ 378/62, 108, 145, 146, 378/147, 150, 158, 153, 156, 157, 158

[56] References Cited

U.S. PATENT DOCUMENTS 4,715,056 12/1987 Vlassbloem et al. ................ 378/146
4,803,714 2/1989 Vlasbloem ............................ 378/62

Primary Examiner—Carolyn E. Fields
Assistant Examiner—David P. Porta
Attorney, Agent, or Firm—Louis E. Marn

[57] ABSTRACT

There are disclosed methods for making radiographs using slit-scanning radiographic techniques wherein a measuring exposure is effected at low radiation intensity and thereafter radiation intensity is set at a value suitable for effecting and taking the actual exposure and further including a modulation of radiation intensity during actual exposure.

4 Claims, 1 Drawing Sheet

METHODS FOR FORMING A RADIOGRAPH USING SLIT RADIOGRAPHY

RELATED APPLICATION

This is a continuation-in-part application of U.S. application Ser. No. 06/648,707, filed Sept. 7, 1984 now U.S. Pat. No. 4,803,714.

BACKGROUND OF THE INVENTION (1) Field of the Invention

This invention relates to slit radiography, and more particularly to methods for forming a radiograph using slit radiography.

(2) Brief Description of the Prior Art

In an article entitled "Schlitzaufnahmetechnik mit mitgeführtem Strahler" by R. Moore and K. Amplatz, published in Elektromedica 1/81, there is disclosed an apparatus comprised of an X-ray source capable of irradiating a patient through a slit diaphragm and having a second slit diaphragm disposed on the other side of the patient whereby the second slit diaphragm permits radiation passing through the patient to pass to an X-ray screen-film combination. In operation, the X-ray source is pivoted along with the first slit diaphragm and the second slit diaphragm, so that the patient is, as it were, scanned strip-wise, and the picture to be formed is built-up in strips.

One advantage of slit-scanning technique, over and above conventional techniques, is that a lower radiation dosage can be used so that the irradiation load on a patient is less, and the effect of scattered radiation can be more effectively suppressed, to produce clearer pictures. A disadvantage of known slit-scanning techniques is that a second slit diaphragm is needed as well as a large X-ray screen.

OBJECTS OF THE INVENTION

An object of the present invention is to provide improved methods for forming radiographs overcoming the disadvantages hereinabove disclosed.

Another object of the present invention is to provide improved methods for forming radiographs at lower radiation dosages.

One important advantage of the invention is that, in the X-ray detector, an intensification can be accomplished by a suitable selection of the electrical field intensity. As a consequence, a lower dosage of radiation can be used.

A further object of the present invention is to provide methods for forming radiographs using slit radiography wherein effects of patient's dimensions are compensated during exposure of the film.

SUMMARY OF THE INVENTION

These and other objects of the present invention are achieved by methods of forming a radiograph of an object using an X-ray source including a slit diaphragm to form a flat X-ray beam wherein the X-ray source during a first scanning of the object at a low level of radiation intensity is used to determine proper setting of the X-ray source for a second scanning of the object for forming a radiograph at a higher energy level whereby the operational setting of the X-ray source is adapted to the specific properties of the body to be examined in a simple manner.

BRIEF DESCRIPTION OF THE DRAWINGS

The invention will be described below in more detail with reference to the accompanying drawings, wherein.

DETAILED DESCRIPTION OF THE DRAWINGS

Figure 1:
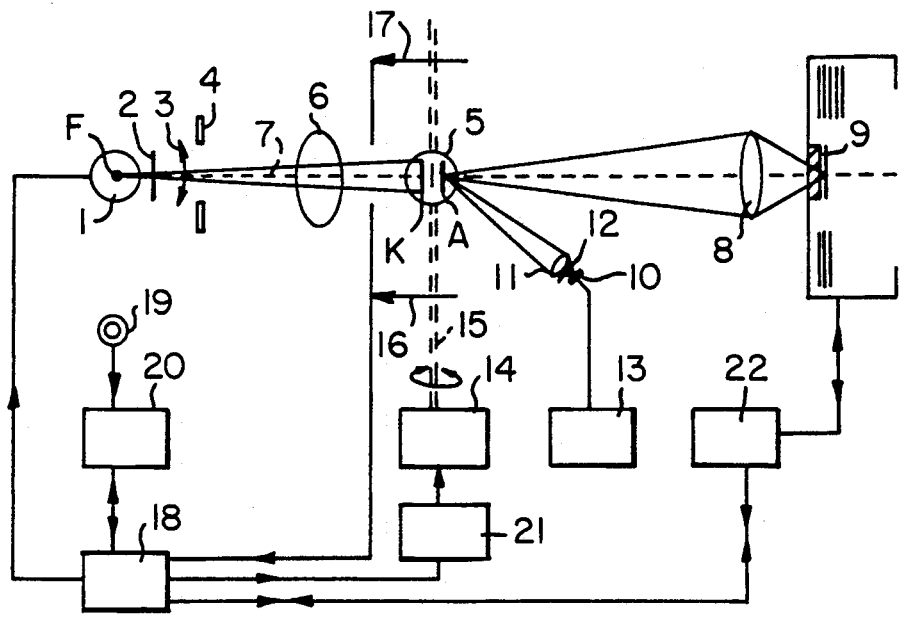
FIG. 1 shows in a schematic view of the slit radiography assembly.

Referring to FIG. 1, there is illustrated an X-ray tube 1 pivotable along with a slit diaphragm 2 about a shaft extending transversely to the plane of the drawing; the axis of the shaft preferably intersects the X-ray focus F mounted in a frame (not shown). Pivotability of the X-ray source and slit diaphragm is indicated by an arrow 3 and a fixed field diaphragm 4.

The X-ray source 1 is arranged in opposition to a case (not shown), which may be closed with a plate of X-ray permeable, but light-opaque material, and in which a special X-ray detector 5 is provided. Between the case and the X-ray source is an open space, in which an object, such as a patient or other object 6 can be placed.

The X-ray detector 5 comprises an elongated housing extending in a direction transverse to the plane of the drawing, in which housing a vacuum prevails, and in which are disposed an elongated cathode K and an elongated anode A parallel thereto. The slit diaphragm 2 has a slit dimension such that X-ray beam 7 exposes the cathode K. The cathode K comprises a layer of material converting incident radiation into light, and a layer of material, which, under the influence of light, emit electrons. The emitted electrons are accelerated under the influence of an electric field established between the cathode and the anode, and passed to the anode, which under the influence of the electrons forms a light image.

The housing of the X-ray detector may consist of glass, or of another material, provided the cathode can be reached by X-rays and, on the anode side, if necessary, a light-permeable window. It is also possible for the anode to be designed, for example, by using a so-called CCD-array, so that it provides image information containing electrical signal that can be stored in a memory for further processing at a later stage. Such detector tube is, in principle, described in Dutch patent application No. 79,00878.

In operation, the X-ray image intensifier moves in synchronism with the sweep of the X-ray source 1, so that the X-ray beam 7 falls at all times on the cathode. It is noted that the X-ray source 1 and the X-ray detector 5 are shown in FIG. 1 in one of the intermediate positions they occupy as a picture is taken. In the inoperative position, the X-ray source 1 is directed diagonally downwardly or diagonally upwardly, and the X-ray detector 5 is in a corresponding position.

If an anode forming a light image is used, the light image formed by the anode in operation is depicted on film 9 by means of an optical system 8. The optical system 8 is disposed so as to be stationary, and the film is also stationary as a picture is taken.

The use of a moving elongated, if desired intensifying, X-ray detector 5 results in several advantages. Thus, a second slit diaphragm of large dimensions moving along with the X-ray source 1 is no longer necessary. Also, it is sufficient to have a relatively small film area (for example 10×10 cm). The exposure of the film 9 can further be controlled in two ways, namely, by controlling the energizing current of the X-ray source 1 sweep and by controlling the voltage between the anode and the cathode of the X-ray detector 5. Finally, the use of an intensifying X-ray detector 5 makes it possible to use very low X-ray dosages.

In order that an optimum X-ray dosage may be selected for a radiograph of an individual patient, according to the present invention, there is first made a measuring exposure. In making a measuring exposure, after the patient or the object to be X-rayed has been placed in position, the X-ray source 1 is energized so that it emits radiation at an intensity level lower by a factor of about 10 than the average intensity level used for normal exposure. The X-ray source 1 moves, for example, from the bottom angular position to the top angular position, with the X-ray image intensifier moving along with it correspondingly. During a certain part of the X-ray image intensifier's path (the measuring field), the average level of the light generated by the anode of the X-ray detector 5 is measured by means of a photometer 10. If an anode is used which generated an electrical signal, an apparatus indicating the average intensity of the electrical signal can be used instead of a photometer. The size of the measuring field can be selected as desired. In experiments, a measuring field of 10×20 cm has proved satisfactory. As, for example for thorax exposures, the X-ray detector 5 should be at least 40 cm long, the measuring field may accordingly be narrower than the field covered by the X-ray detector 5 without any objections.

In front of the photometer, a lens system 11 and a diaphragm 12 may be placed. The photometer 10 is connected to an instrument 13 to be read. Depending on the light value measured, the X-ray dosage needed for the actual exposure can now be set at an optimum value either manually or automatically. In the latter case, the output signal from the photometer controls the voltage of the X-ray detector 5 or the current through the X-ray tube 1. The readable instrument then only serves for monitoring purposes and, if desired, may be omitted. It is noted that the measuring exposure takes place without a film 9. The film is not supplied until the actual exposure. When the X-ray source 1 is properly set, the X-ray source 1 is pivoted in the opposite direction, with the X-ray detector 5 moving along with it for making the actual radiograph.

For monitoring purposes, the photometer can be switched on again during the actual exposure. For this purpose, after the measuring exposure, the photometer is first set in the zero position, and also set in a less sensitive mode. After the actual exposure or before the next measuring exposure, too, the photometer is re-set in the zero position. Generally, the making of a radiograph including measuring exposure is effected in about ten seconds.

Figure 2:
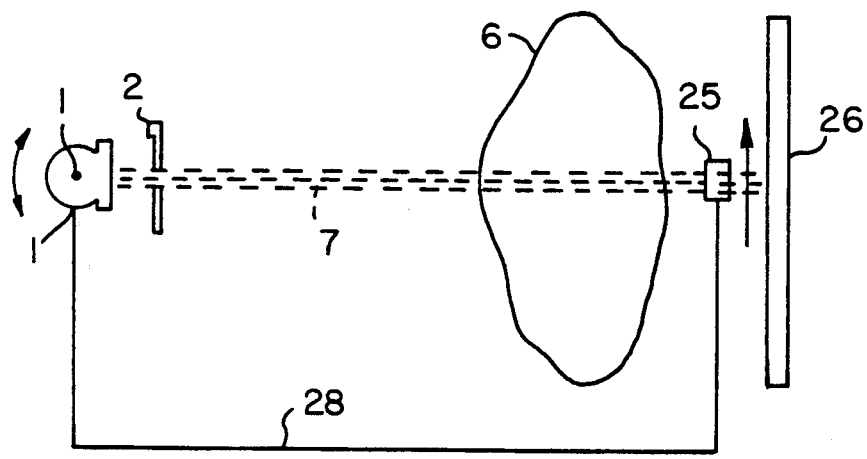
FIG. 2 is a schematic view of one method for forming a radiograph.

In the method of forming a radiograph as illustrated in FIG. 2, a dosimeter 25, such as described in either copending U.S. application Ser. Nos. 06/931,538 or 06/931,539, filed Nov. 14, 1986, the substance of which is hereby incorporated by reference, is used in lieu of the X-ray detector 5. Accordingly, the measuring step, as hereinabove described with reference to FIG. 1, is effected during which time a large X-ray film 9 (not shown) disposed in a cassette 26 is covered (or is subsequently positioned in the cassette) whereby the dosimeter 25 measures radiation intensity levels. The exposure step is effected with or without concomitant scanning with the dosimeter with the X-ray film 9 being uncovered (or positioned) in the cassette 26 to permit exposure thereof to imaging radiation wherein the energizing level of the X-ray source 1 is varied in accordance with the results of the dosimeter during the measuring step.

Figure 3:
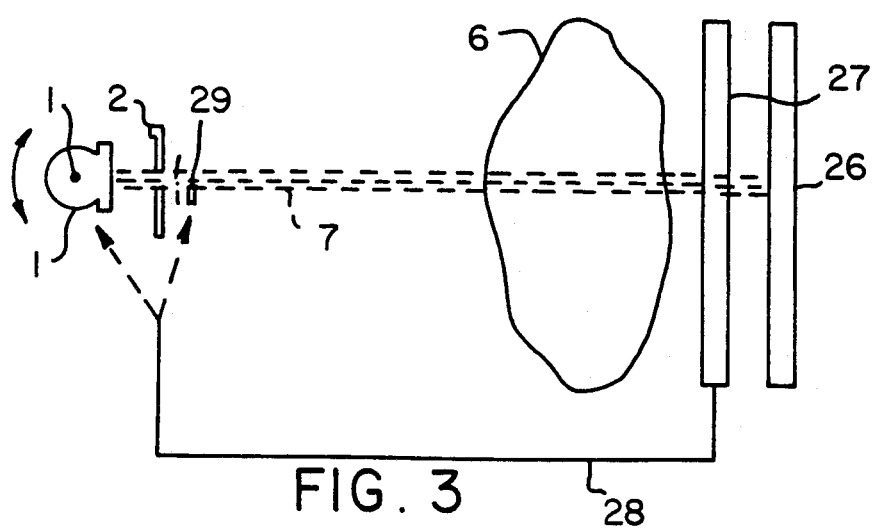
FIG. 3 is a schematic view of another method for forming a radiograph.

The method of FIG. 3 is effected with a two-dimensional dosimeter 27, i.e. of like dimension to the X-ray film cassette 26, wherein the dosimeter 27 provides measuring signals 28 during the measuring or first scanning step. Such measuring signals 28 are likewise used to vary the energizing level of the X-ray source 1 during exposure of the X-ray film.

The slit diaphragm assembly of FIG. 3 may be provided with an attenuating assembly 29, formed of a plurality of beam sector modulators (not shown), such as disclosed in copending U.S. application Ser. No. 06/875,409, filed Jun. 17, 1986, the substance of which is incorporated herein by references, wherein the measuring signals 28 obtained from the dosimeter 27 during the initial low level measuring step is used during the subsequent exposure step to control the beam sector modulators or attenuating elements at the setting (i.e., MA-setting or voltage setting) of the X-ray source 1 as determined during the measuring step. The measuring signals 28 obtained during the measuring step or first scanning run are not used to effect the beam sector modulator but are used to determine intensity level of the X-ray source 1. During the imaging step or second scanning, the measuring signals 28 obtained from the dosimeter 27 are applied or used for controlling the beam sector modulators of the attenuating assembly 29.

While the invention has been described in connection with an exemplary embodiment thereof, it will be understood that many modifications will be apparent to those of ordinary skill in the art; and that this application is intended to cover any adaptations of variations thereof. Therefore, it is manifestly intended that this invention be only limited by the claims and the equivalents thereof.

What is claimed is:

1. A method for forming a radiograph of an object, which comprises the steps of:
   (a) energizing an X-ray source to a first level of radiation intensity, said X-ray source including a slit diaphragm;
   (b) effecting a first scanning of said object by an X-ray beam from said X-ray source;
   (c) generating output signals of radiation intensity from an elongated X-ray detector during said first scanning;
   (d) measuring said output signals during at least a portion of said first scanning;
   (e) energizing said X-ray beam to a higher level of radiation intensity as determined by step (d) for forming a radiograph of said object;
   (f) effecting a second scanning of said object with an X-ray beam from said X-ray source at said higher level of radiation intensity;
   (g) modulating said X-ray beam during said second scanning; and
   (h) forming said radiograph during said second scanning.

2. The method for forming a radiograph of an object as defined in claim 1 wherein said X-ray detector measures ionizing radiation.

3. The method for forming a radiograph of an object as defined in claim 1 wherein said modulating step (g) is effected in response to said output signals of step (d).

4. The method for forming a radiograph of an object as defined in claim 1 and further including the steps of generating output signals of radiation intensity from said elongated X-ray detector during said second scanning and modulating said X-ray beam during said second scanning in response to said output signals generated during said second scanning.

* * * * *